(12) United States Patent
Loughran, Jr. et al.

(10) Patent No.: US 9,353,417 B1
(45) Date of Patent: May 31, 2016

(54) METHOD OF DIAGNOSING LARGE GRANULAR LYMPHOCYTE LEUKEMIA USING ALTERNATIVE SPLICE VARIANTS OF SERINE PROTEASES

(71) Applicants: Thomas P. Loughran, Jr., Hummelstown, PA (US); Ravi Kothapalli, Wesley Chapel, FL (US)

(72) Inventors: Thomas P. Loughran, Jr., Hummelstown, PA (US); Ravi Kothapalli, Wesley Chapel, FL (US)

(73) Assignee: University of South Florida, Tampa, FL (US)

( * ) Notice: Subject to any disclaimer, the term of this patent is extended or adjusted under 35 U.S.C. 154(b) by 113 days.

(21) Appl. No.: 14/069,815

(22) Filed: Nov. 1, 2013

Related U.S. Application Data

(63) Continuation of application No. 10/905,242, filed on Dec. 22, 2004, now abandoned.

(60) Provisional application No. 60/481,825, filed on Dec. 22, 2003.

(51) Int. Cl.
*C12Q 1/68* (2006.01)
*C12P 19/34* (2006.01)

(52) U.S. Cl.
CPC .................................. *C12Q 1/6886* (2013.01)

(58) Field of Classification Search
None
See application file for complete search history.

(56) References Cited

PUBLICATIONS

Kothapalli et al; BMC Bioinformatics, vol. 3, 2002, pp. 1-10.*

* cited by examiner

*Primary Examiner* — Jehanne Sitton
(74) *Attorney, Agent, or Firm* — Michele L. Lawson; Robert J. Varkonyi; Smith & Hopen, P.A.

(57) ABSTRACT

Methods of diagnosing large granular lymphocytic leukemia are provided herein. Novel splice variants of Granzyme B and Granzyme H as well as methods for screening for compositions regulating the splice variants and the development of therapeutic agents for the modulation thereof are also provided herein. Regulation of the splice variants is useful in the treatment of leukemic LGL, where these isoforms are constitutively over-expressed.

4 Claims, 5 Drawing Sheets

Schematic Diagram showing splice variants of Granzyme B

A: Granzyme B wilde type; B: cryptic variants; C: Granzyme B variant 1; D: Granzyme variant 2 ns, in which:

SEQUENCE LISTING

```
<160> NUMBER OF SEQ ID NOS: 15

<210> SEQ ID NO 1
<211> LENGTH: 916
<212> TYPE: DNA
<213> ORGANISM: Homo sapiens

<400> SEQUENCE: 1
ggcacgaggc tgagaagatg caaccaatcc tgcttctgct ggccttcctc ctgctgccca      60
gggcagatgc agactttcc ttcaggggag atcatcgggg gacatgaggc caagccccac     120
tcccgcccct acatggctta tcttatgatc tgggatcaga agtctctgaa gaggtgcggt     180
ggcttcctga tacaagacga cttcgtgctg acagctgctc actgttgggg aagctccata     240
aatgtcacct tgggggccca caatatcaaa gaacaggagc cgacccagca gtttatccct     300
gtgaaaagac ccatccccca tccagcctat aatcctaaga acttctccaa cgacatcatg     360
ctactgcagc tggagagaaa ggccaagcgg accagagctg tgcagcccct caggctacct     420
agcaacaagg cccaggtgaa gccagggcag acatgcagtg tggccggctg ggggcagacg     480
```

| | |
|---|---:|
| gccccctgg gaaaacactc acacacacta caagaggtga agatgacagt gcaggaagat | 540 |
| cgaaagtgcg aatctgactt acgccattat tacgacagta ccattgagtt gtgcgtgggg | 600 |
| gacccagaga ttaaaaagac ttcctttaag ggggactctg gaggccctct tgtgtgtaac | 660 |
| aaggtggccc agggcattgt ctcctatgga cgaaacaatg gcatgcctcc acgagcctgc | 720 |
| accaaagtct caagctttgt acactggata agaaaaccca tgaaacgcta ctaactacag | 780 |
| gaagcaaact aagccccgc tgtaatgaaa caccttctct ggagccaagt ccagatttac | 840 |
| actgggagag gtgccagcaa ctgaataaat acctcttagc tgagtggaaa aaaaaaaaa | 900 |
| aaaaaaaaag ctcgta | 916 |

<210> SEQ ID NO 2
<211> LENGTH: 676
<212> TYPE: DNA
<213> ORGANISM: Homo sapiens

<400> SEQUENCE: 2

| | |
|---|---:|
| cttatgcaac caatcctgct tctgctggcc ttcctcctgc tgcccagggc agatgcaggg | 60 |
| gagatcatcg ggggacatga ggccaagccc cactcccgcc cctacatggc ttatcttatg | 120 |
| atctgggatc agaagtctct gaagaggtgc ggtggcttcc tgatacgaga cgacttcgtg | 180 |
| ctgacagctg ctcactgttg gggaagcctg gagagaaagg ccaagcggac cagagctgtg | 240 |
| cagcccctca ggctacctag caacaaggcc caggtgaagc cagggcagac atgcagtgtg | 300 |
| gccggctggg ggcagacggc ccccctggga aaacactcac acacactaca agaggtgaag | 360 |
| atgacagtgc aggaagatcg aaagtgcgaa tctgacttac gccattatta cgacagtacc | 420 |
| attgagttgt gcgtggggga cccagagatt aaaaagactt cctttaaggg ggactctgga | 480 |
| ggccctcttg tgtgtaacaa ggtggcccag ggcattgtct cctatggacg aaacaatggc | 540 |
| atgcctccac gagcctgcac caaagtctca agctttgtac actggataaa gaaaaccatg | 600 |
| aaacgctact aactacagga agcaaactaa gccccgctg taatgaaaca ccttctctaa | 660 |
| gggcgaattc gtttaa | 676 |

<210> SEQ ID NO 3
<211> LENGTH: 531
<212> TYPE: DNA
<213> ORGANISM: Homo sapiens

<400> SEQUENCE: 3

| | |
|---|---:|
| cccctttatgc aaccaatcct gcttctgctg gccttcctcc tgctgcccag ggcagatcag | 60 |
| ctggagagaa aggccaagcg gaccagagct gtgcagcccc tcaggctacc tagcaacaag | 120 |
| gcccaggtga agccagggca gacatgcagt gtggccggct gggggcagac ggccccctg | 180 |
| ggaaaacact cacacacact acaagaggtg aagatgacag tgcaggaaga tcgaaagtgc | 240 |
| gaatctgact tacgccatta ttacgacagt accattgagt tgtgcgtggg gacccagag | 300 |
| attaaaaaga cttcctttaa ggggactct ggaggccctc ttgtgtgtaa caaggtggcc | 360 |
| cagggcattg tctcctatgg acgaaacaat ggcatgcctc cacgagcctg caccaaagtc | 420 |
| tcaagctttg tacactggat aaagaaaacc atgaaacgct actaactaca ggaagcaaac | 480 |
| taagccccg ctgtaatgaa acaccttctc taagggcgaa ttcgtttaaa c | 531 |

<210> SEQ ID NO 4
<211> LENGTH: 632
<212> TYPE: DNA
<213> ORGANISM: Homo sapiens -continued

<400> SEQUENCE: 4

```
tttctggaag gagtcaacac caacagctct gacctgggca gccttcctga gaaaatgcag    60
ccattcctcc tcctgttggc cttttcttctg accctgggg ctgggacaga ggagatcatc   120
gggggccatg aggccaagcc ccactcccgc ccctacatgg cctttgttca gtttctgcaa   180
gagaagagtc ggaagaggtg tggcggcatc ctagtgagaa aggactttgt gctgacagct   240
gctcactgcc agggaagggg ggactccggg gggcccctcg tgtgtaagga cgtagcccaa   300
ggtattctct cctatggaaa caaaaagggg acacctccag gagtctacat caaggtctca   360
cacttcctgc cctggataaa gagaacaatg aagcgcctct aacagcaggc atgagactaa   420
ccttcctctg ggcctgacca tctctgggac agaggcaaga atccccaagg ggtgggcagt   480
cggggttgca ggactgtaat aaatggatct ctggtgtaaa aaaaaaaaaa aaaaaaaaa    540
aacctcgagg gggggcccgg tacccaattc gccctatagt gagtcgtatt acaattcact   600
gggccgtcgt tttacaacgt cgtgactggg aa                                 632
```

<210> SEQ ID NO 5
<211> LENGTH: 711
<212> TYPE: DNA
<213> ORGANISM: Homo sapiens

<400> SEQUENCE: 5

```
cggcacgagg cccatccctc cttcatctcc ctccagcatt tgtttctgga aggagtcaac    60
accaacagct ctgacctggg cagccttcct gagaaaatgc agccattcct cctcctgttg   120
gccttttcttc tgacccctgg ggctgggaca gaggagatca tcgggggcca tgaggccaag   180
ccccactccc gccctactat ggcctttgtt cagtttctgc aagagaagag tcggaagagg   240
tgtggcggca tcctagtgag aaaggacttt gtgctgacag ctgctcactg ccagggaagc   300
tccataaatg tcaccttggg ggcccacaat atcaaggaac aggagcggac ccagcagttt   360
atccctgtga aaagacccat cccccatcca gcctataatc ctaagaactt ctccaacgac   420
atcatgctac tgcaggggga ctccgggggg ccctcgtgt gtaaggacgt agcccaaggt   480
attctctcct atggaaacaa aaagggaca cctccaggag tctacatcaa ggtctcacac   540
ttcctgccct ggataaagag aacaatgaag cgcctctaac agcaggcatg agactaacct   600
tcctctgggc ctgaccatct ctgggacaga ggcaagaatc cccaagggt gggcagtcgg   660
ggttgcagga ctgtaataaa tggatctctg gtgtgaaaaa aaaaaaaaa a             711
```

<210> SEQ ID NO 6
<211> LENGTH: 18
<212> TYPE: DNA
<213> ORGANISM: Artificial Sequence
<220> FEATURE:
<223> OTHER INFORMATION: Forward Primer

<400> SEQUENCE: 6

```
tgcaaccaat cctgcttc                                                   18
```

<210> SEQ ID NO 7
<211> LENGTH: 21
<212> TYPE: DNA
<213> ORGANISM: Artificial Sequence
<220> FEATURE:
<223> OTHER INFORMATION: Reverse Primer

<400> SEQUENCE: 7

```
agagaaggtg tttcatcaca g                                            21

<210> SEQ ID NO 8
<211> LENGTH: 24
<212> TYPE: DNA
<213> ORGANISM: Artificial Sequence
<220> FEATURE:
<223> OTHER INFORMATION: Forward Primer

<400> SEQUENCE: 8
tttgtgctga cagctgctca ctgt                                         24

<210> SEQ ID NO 9
<211> LENGTH: 27
<212> TYPE: DNA
<213> ORGANISM: Artificial Sequence
<220> FEATURE:
<223> OTHER INFORMATION: Reverse Primer

<400> SEQUENCE: 9
ggaaggttag tctcatgcct gctgtta                                      27

<210> SEQ ID NO 10
<211> LENGTH: 55
<212> TYPE: DNA
<213> ORGANISM: Homo sapiens

<400> SEQUENCE: 10
tgcccagggc agatgcagac ttttccttca ggggagatca tcggggaca tgagg        55

<210> SEQ ID NO 11
<211> LENGTH: 235
<212> TYPE: PRT
<213> ORGANISM: Homo sapiens

<400> SEQUENCE: 11
```

| | | | | | | | | | | | | | | |
|---|---|---|---|---|---|---|---|---|---|---|---|---|---|---|
| Met | Gln | Thr | Phe | Pro | Ser | Gly | Glu | Ile | Ile | Gly | Gly | His | Glu | Ala | Lys |
| 1 | | | | 5 | | | | | 10 | | | | | 15 | |
| Pro | His | Ser | Arg | Pro | Tyr | Met | Ala | Tyr | Leu | Met | Ile | Trp | Asp | Gln | Lys |
| | | | 20 | | | | | 25 | | | | | 30 | | |
| Ser | Leu | Lys | Arg | Cys | Gly | Gly | Phe | Leu | Ile | Gln | Asp | Asp | Phe | Val | Leu |
| | | 35 | | | | | 40 | | | | | 45 | | | |
| Thr | Ala | Ala | His | Cys | Trp | Gly | Ser | Ser | Ile | Asn | Val | Thr | Leu | Gly | Ala |
| | 50 | | | | | 55 | | | | | 60 | | | | |
| His | Asn | Ile | Lys | Glu | Gln | Glu | Pro | Thr | Gln | Gln | Phe | Ile | Pro | Val | Lys |
| 65 | | | | | 70 | | | | | 75 | | | | | 80 |
| Arg | Pro | Ile | Pro | His | Pro | Ala | Tyr | Asn | Pro | Lys | Asn | Phe | Ser | Asn | Asp |
| | | | | 85 | | | | | 90 | | | | | 95 | |
| Ile | Met | Leu | Leu | Gln | Leu | Glu | Arg | Lys | Ala | Lys | Arg | Thr | Arg | Ala | Val |
| | | | 100 | | | | | 105 | | | | | 110 | | |
| Gln | Pro | Leu | Arg | Leu | Pro | Ser | Asn | Lys | Ala | Gln | Val | Lys | Pro | Gly | Gln |
| | | | 115 | | | | | 120 | | | | | 125 | | |
| Thr | Cys | Ser | Val | Ala | Gly | Trp | Gly | Gln | Thr | Ala | Pro | Leu | Gly | Lys | His |
| | 130 | | | | | 135 | | | | | 140 | | | | |
| Ser | His | Thr | Leu | Gln | Glu | Val | Lys | Met | Thr | Val | Gln | Glu | Asp | Arg | Lys |
| 145 | | | | | 150 | | | | | 155 | | | | | 160 |
| Cys | Glu | Ser | Asp | Leu | Arg | His | Tyr | Tyr | Asp | Ser | Thr | Ile | Glu | Leu | Cys |
| | | | | 165 | | | | | 170 | | | | | 175 | |
| Val | Gly | Asp | Pro | Glu | Ile | Lys | Lys | Thr | Ser | Phe | Lys | Gly | Asp | Ser | Gly |
| | | | 180 | | | | | 185 | | | | | 190 | | |

```
Gly Pro Leu Val Cys Asn Lys Val Ala Gln Gly Ile Val Ser Tyr Gly
            195                 200                 205

Arg Asn Asn Gly Met Pro Pro Arg Ala Cys Thr Lys Val Ser Ser Phe
210                 215                 220

Val His Trp Ile Lys Lys Thr Met Lys Arg Tyr
225                 230                 235

<210> SEQ ID NO 12
<211> LENGTH: 202
<212> TYPE: PRT
<213> ORGANISM: Homo sapiens

<400> SEQUENCE: 12

Met Gln Pro Ile Leu Leu Leu Ala Phe Leu Leu Pro Arg Ala
1               5                   10                  15

Asp Ala Gly Glu Ile Ile Gly Gly His Glu Ala Lys Pro His Ser Arg
                20                  25                  30

Pro Tyr Met Ala Tyr Leu Met Ile Trp Asp Gln Lys Ser Leu Lys Arg
            35                  40                  45

Cys Gly Gly Phe Leu Ile Arg Asp Asp Phe Val Leu Thr Ala Ala His
        50                  55                  60

Cys Trp Gly Ser Leu Glu Arg Lys Ala Lys Arg Thr Arg Ala Val Gln
65                  70                  75                  80

Pro Leu Arg Leu Pro Ser Asn Lys Ala Gln Val Lys Pro Gly Gln Thr
                85                  90                  95

Cys Ser Val Ala Gly Trp Gly Gln Thr Ala Pro Leu Gly Lys His Ser
            100                 105                 110

His Thr Leu Gln Glu Val Lys Met Thr Val Gln Glu Asp Arg Lys Cys
        115                 120                 125

Glu Ser Asp Leu Arg His Tyr Tyr Asp Ser Thr Ile Glu Leu Cys Val
    130                 135                 140

Gly Asp Pro Glu Ile Lys Lys Thr Ser Phe Lys Gly Asp Ser Gly Gly
145                 150                 155                 160

Pro Leu Val Cys Asn Lys Val Ala Gln Gly Ile Val Ser Tyr Gly Arg
                165                 170                 175

Asn Asn Gly Met Pro Pro Arg Ala Cys Thr Lys Val Ser Ser Phe Val
            180                 185                 190

His Trp Ile Lys Lys Thr Met Lys Arg Tyr
        195                 200

<210> SEQ ID NO 13
<211> LENGTH: 152
<212> TYPE: PRT
<213> ORGANISM: Homo sapiens

<400> SEQUENCE: 13

Met Gln Pro Ile Leu Leu Leu Ala Phe Leu Leu Pro Arg Ala
1               5                   10                  15

Asp Gln Leu Glu Arg Lys Ala Lys Arg Thr Arg Ala Val Gln Pro Leu
                20                  25                  30

Arg Leu Pro Ser Asn Lys Ala Gln Val Lys Pro Gly Gln Thr Cys Ser
            35                  40                  45

Val Ala Gly Trp Gly Gln Thr Ala Pro Leu Gly Lys His Ser His Thr
        50                  55                  60

Leu Gln Glu Val Lys Met Thr Val Gln Glu Asp Arg Lys Cys Glu Ser
65                  70                  75                  80
```

Asp Leu Arg His Tyr Tyr Asp Ser Thr Ile Glu Leu Cys Val Gly Asp
            85                  90                  95

Pro Glu Ile Lys Lys Thr Ser Phe Lys Gly Asp Ser Gly Pro Leu
            100                 105                 110

Val Cys Asn Lys Val Ala Gln Gly Ile Val Ser Tyr Gly Arg Asn Asn
            115                 120                 125

Gly Met Pro Pro Arg Ala Cys Thr Lys Val Ser Ser Phe Val His Trp
        130                 135                 140

Ile Lys Lys Thr Met Lys Arg Tyr
145                 150

<210> SEQ ID NO 14
<211> LENGTH: 115
<212> TYPE: PRT
<213> ORGANISM: Homo sapiens

<400> SEQUENCE: 14

Met Gln Pro Phe Leu Leu Leu Ala Phe Leu Leu Thr Pro Gly Ala
1               5                   10                  15

Gly Thr Glu Glu Ile Ile Gly Gly His Glu Ala Lys Pro His Ser Arg
            20                  25                  30

Pro Tyr Met Ala Phe Val Gln Phe Leu Gln Glu Lys Ser Arg Lys Arg
        35                  40                  45

Cys Gly Gly Ile Leu Val Arg Lys Asp Phe Val Leu Thr Ala Ala His
    50                  55                  60

Cys Gln Gly Arg Gly Asp Ser Gly Gly Pro Leu Val Cys Lys Asp Val
65                  70                  75                  80

Ala Gln Gly Ile Leu Ser Tyr Gly Asn Lys Lys Gly Thr Pro Pro Gly
                85                  90                  95

Val Tyr Ile Lys Val Ser His Phe Leu Pro Trp Ile Lys Arg Thr Met
            100                 105                 110

Lys Arg Leu
        115

<210> SEQ ID NO 15
<211> LENGTH: 160
<212> TYPE: PRT
<213> ORGANISM: Homo sapiens

<400> SEQUENCE: 15

Met Gln Pro Phe Leu Leu Leu Ala Phe Leu Leu Thr Pro Gly Ala
1               5                   10                  15

Gly Thr Glu Glu Ile Ile Gly Gly His Glu Ala Lys Pro His Ser Arg
            20                  25                  30

Pro Tyr Met Ala Phe Val Gln Phe Leu Gln Glu Lys Ser Arg Lys Arg
        35                  40                  45

Cys Gly Gly Ile Leu Val Arg Lys Asp Phe Val Leu Thr Ala Ala His
    50                  55                  60

Cys Gln Gly Ser Ser Ile Asn Val Thr Leu Gly Ala His Asn Ile Lys
65                  70                  75                  80

Glu Gln Glu Arg Thr Gln Gln Phe Ile Pro Val Lys Arg Pro Ile Pro
                85                  90                  95

His Pro Ala Tyr Asn Pro Lys Asn Phe Ser Asn Asp Ile Met Leu Leu
            100                 105                 110

Gln Gly Asp Ser Gly Gly Pro Leu Val Cys Lys Asp Val Ala Gln Gly
        115                 120                 125

```
Ile Leu Ser Tyr Gly Asn Lys Lys Gly Thr Pro Pro Gly Val Tyr Ile
    130                 135                 140

Lys Val Ser His Phe Leu Pro Trp Ile Lys Arg Thr Met Lys Arg Leu
145                 150                 155                 160
```

METHOD OF DIAGNOSING LARGE GRANULAR LYMPHOCYTE LEUKEMIA USING ALTERNATIVE SPLICE VARIANTS OF SERINE PROTEASES

CROSS-REFERENCE TO RELATED APPLICATIONS

This application claims priority to currently pending U.S. Nonprovisional application Ser. No. 10/905,242, entitled "Characterization of Alternative Splice Variants of Serine Proteases in Large Granular Lymphocyte Leukemia", filed Dec. 22, 2004, which claims priority to U.S. Provisional Patent Application No. 60/481,825, entitled "Characterization of Alternative Splice Variants of Serine Proteases in Large Granular Lymphocyte Leukemia", filed on Dec. 22, 2003, the contents of each of which are hereby incorporated by reference.

BACKGROUND OF THE INVENTION

Granzymes are serine proteases present in secretory granules of cytolytic T cells and natural killer (NK) cells (Bleackley et al, 1988, Jenne, 1988). Granzyme B and A along with perforin have been implicated in cell-mediated cytotoxicity (Bleackley et al, 1988, Jenne, 1988). These granzymes were purified from human T cell lines and from short-term cultures of activated human PBMCs (Hameed et al, 1988, Krahenbuhl et al, 1988, Poe Ct al, 1998, Poe et al, 1991).

Recently, the three dimensional structure of Granzyme B was established (Waugh et al, 2000). Granzyme B has an Aspase activity (Poe et al., 1991, Powers and Kam, 1995) whereas granzyme A has tryptase activity (Peitsh and Tschopp, 1994). Much progress has been made in understanding the molecular mechanisms of granzyme B associated apoptosis in target cells (Russel and Timothy, 2002). Granzyme B can cause apoptosis of target cells by both caspase dependent and caspase independent mechanisms (Talania, 1997, Thomas et al, 2000, Alimonti J B, 2001).

Very little is known about the mechanism of granzyme A in inducing cell death. (Pinkoski et al, 2003). Although granzyme H was identified in activated T-cells and found to have chymase activity, nothing is known about its role in target cell death (Haddad, 1991; Edwards et al., 1999).

SUMMARY OF THE INVENTION

Serine proteases such as granzyme B and A are expressed mainly by cytotoxic T lymphocytes (CTL) and natural killer (NK) cells. These granzymes are essential components of the granules exocytosis pathway. This is a major pathway by which cytotoxic T lymphocytes and natural killer cells induce cell death in a target. Granzyme B gene is induced in activated lymphocytes upon antigenic stimulation and it has aspase activity. Granzyme H is a close structural relative of granzyme B and shown 71% amino acid identity with it. Human granzyme H is a chymase that is highly expressed in the NK cell compartment. This gene encodes it lies between granzyme B and cathepsin G. Recently, we found that granzyme H is also constitutively over-expressed in LGL leukemic cells along with granzyme B. Both Granzyme B and H have 5 exons. The structures of these genes were thoroughly studied at mRNA level and also at protein level. Granzyme B proteolytically activates several caspases resulting in DNA fragmentation and in the rapid apoptotic death of the target cell. Granzyme B also has shown to directly cause apoptosis independent of caspases. In the present study by screening LGL leukemia library and also by performing RT-PCR, the inventors identified different isoforms of both granzyme B and granzyme H. In leukemic LGL, these isoforms are constitutively over-expressed. Upon activation of PBMC with IL-2 and PHA resulted in up-regulation of only granzyme B isoforms but not Granzyme H isoforms.

The inventors have identified constitutive expression of granzyme H in large granular lymphocyte leukemia (Kothapalli et al, 2003). Both granzyme B and granzyme H each have five exons separated by four introns. These are localized in close proximity on chromosome 14. It is intriguing that these genes are closely linked to the T-cell receptor x and chain receptor locus. This is where most detectable chromosomal translocations and inversions take place in human T-cell leukemias and lymphomas (Croce et al, 1985; Harper et al, 1988). The inventors identified several alternative splice variants of granzyme B and granzyme H in LGL leukemia and also in activated PBMCs.

The present invention provides isolated and purified polynucleotides encoding Granzyme B variant polypeptides. In certain embodiments the isolated and purified polynucleotide encoding a polypeptide includes the amino acid sequence of amino acids 1 through 235 set forth in SEQ ID NO: 11. In additional embodiments the polynucleotide includes the nucleotide sequence of nucleotides 67 through 771 set forth in SEQ ID NO: 1.

BRIEF DESCRIPTION OF THE DRAWINGS

For a fuller understanding of the nature and objects of the invention, reference should be made to the following detailed description, taken in connection with the accompanying drawings, in which:

FIG. 4A: Granzyme B wild type; 4B: Cryptic variant; 4C: Granzyme B variant 1; 4D: Granzyme B variant 2.

FIG. 5A: Granzyme H wild type; 5B Granzyme H splice variant 2; 5C: Granzyme H splice variant 3.

DETAILED DESCRIPTION OF THE PREFERRED EMBODIMENT

Figure 1:
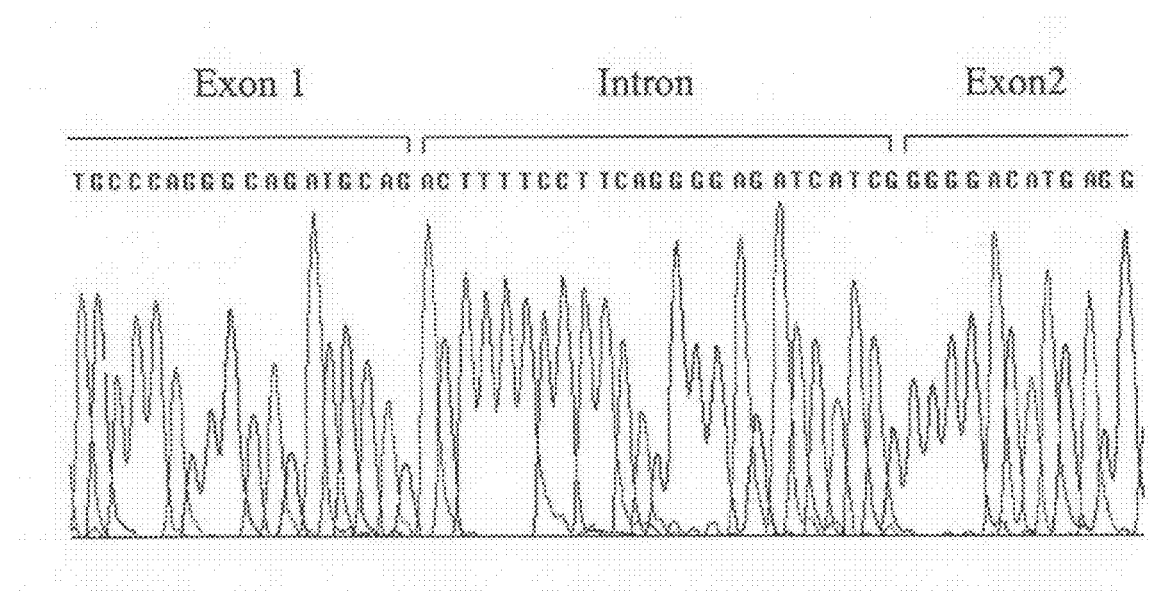
FIG. 1 is the nucleotide sequence (SEQ ID NO: 10) showing the portion of extra nucleotides retained from intron in Granzyme B.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

A "variant" of Granzyme B and/or Granzyme H, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

"Granzyme B variants" and "Granzyme H variants", as used herein, refer to the amino acid sequences of substantially purified Granzyme B variants and Granzyme H variants obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to Granzyme B variants and Granzyme H variants, increases or prolongs the duration of the effect of Granzyme B variants and Granzyme H variants. Agonists may include proteins, nucleic acids, carbohydrates, or any other molecules which bind to and modulate the effect of Granzyme B variants and Granzyme H variants.

An "allele" or "allelic sequence", as used herein, is an alternative form of the gene encoding Granzyme B variants and Granzyme H variants. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding Granzyme B variants and Granzyme H variants as used herein include those with deletions, insertions, or substitutions of different nucleotides resulting in a polynucleotide that encodes the same or a functionally equivalent Granzyme B variants and Granzyme H variants. Included within this definition are polymorphisms which may or may not be readily detectable using a particular oligonucleotide probe of the polynucleotide encoding Granzyme B variants and Granzyme H variants, and improper or unexpected hybridization to alleles, with a locus other than the normal chromosomal locus for the polynucleotide sequence encoding Granzyme B variants and Granzyme H variants. The encoded protein may also be "altered" and contain deletions, insertions, or substitutions of amino acid residues which produce a silent change and result in a functionally equivalent Granzyme B variants and Granzyme H variants. Deliberate amino acid substitutions may be made on the basis of similarity in polarity, charge, solubility, hydrophobicity, hydrophilicity, and/or the amphipathic nature of the residues as long as the biological or immunological activity of Granzyme B variants and Granzyme H variants is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein, refers to an oligopeptide, peptide, polypeptide, or protein sequence, and fragment thereof, and to naturally occurring or synthetic molecules. Fragments of Granzyme B variants and Granzyme H variants are preferably about 5 to about 15 amino acids in length and retain the biological activity or the immunological activity of Granzyme B variants and Granzyme H variants. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) PCR Primer, a Laboratory Manual, Cold Spring Harbor Press, Plainview, N.Y.).

The term "antagonist", as used herein, refers to a molecule which, when bound to Granzyme B variants and Granzyme H variants, decreases the amount or the duration of the effect of the biological or immunological activity of Granzyme B variants and Granzyme H variants. Antagonists may include proteins, nucleic acids, carbohydrates, antibodies or any other molecules which decrease the effect of Granzyme B variants and Granzyme H variants.

As used herein, the term "antibody" refers to intact molecules as well as fragments thereof, such as Fab, F(ab')2, and Fv, which are capable of binding the epitopic determinant. Antibodies that bind Granzyme B variants and Granzyme H variants polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic Granzyme B variants and Granzyme H variants, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A--G--T" binds to the complementary sequence "T--C--A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding Granzyme B variants and Granzyme H variants (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

The term "correlates with expression of a polynucleotide", as used herein, indicates that the detection of the presence of ribonucleic acid that is similar to SEQ ID NO:2 by northern analysis is indicative of the presence of mRNA encoding Granzyme B variants and Granzyme H variants in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to Granzyme B variants and Granzyme H variants or the encoded Granzyme B variants and Granzyme H variants. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345-355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of Granzyme B variants and Granzyme H variants. For example, modulation may cause an increase or a decrease in protein activity, binding characteristics, or any other biological, functional or immunological properties of Granzyme B variants and Granzyme H variants.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53-63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length Granzyme B variants and Granzyme H variants and fragments thereof.

The term "sample", as used herein, is used in its broadest sense. A biological sample suspected of containing nucleic acid encoding Granzyme B variants and Granzyme H variants, or fragments thereof, or Granzyme B variants and Granzyme H variants itself may comprise a bodily fluid, extract from a cell, chromosome, organelle, or membrane isolated from a cell, a cell, genomic DNA, RNA, or cDNA (in solution or bound to a solid support, a tissue, a tissue print, and the like.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell.

It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The invention is based on the discovery of a new human splice variants (hereinafter referred to as "Granzyme B variants" and/or "Granzyme H variants"), the polynucleotides encoding Granzyme B variants and Granzyme H variants, and the use of these compositions for the diagnosis, prevention, or treatment of developmental, neoplastic, and immunological disorders.

In one embodiment, the invention encompasses a polynucleotide comprising the nucleic acid sequence (SEQ ID NO: 1) encoding Granzyme B Cryptic Variant. Granzyme B Cryptic variant is 235 amino acids in length.

In one embodiment, the invention encompasses a polynucleotide comprising the nucleic acid sequence (SEQ ID NO: 2) encoding Granzyme B Variant1. Granzyme B Variant1 is 202 amino acids in length.

In one embodiment, the invention encompasses a polynucleotide comprising the nucleic acid sequence (SEQ ID NO: 3) encoding Granzyme B Variant2. Granzyme B Variant2 is 152 amino acids in length.

In one embodiment, the invention encompasses a polynucleotide comprising the nucleic acid sequence (SEQ ID NO: 4) encoding Granzyme H Variant2 (isoform). Granzyme H Variant2 (isoform) is 115 amino acids in length.

In one embodiment, the invention encompasses a polynucleotide comprising the nucleic acid sequence (SEQ ID NO:5) encoding Granzyme H Variant3 (isoform). Granzyme H Variant3 is 160 amino acids in length.

The invention also encompasses Granzyme B variants and Granzyme H variants. A preferred Granzyme B variant and Granzyme H variant is one having at least 80%, and more preferably at least 90%, amino acid sequence identity to the Granzyme B and Granzyme H amino acid sequences and which retains at least one biological, immunological or other functional characteristic or activity of Granzyme B and Granzyme H. A most preferred Granzyme B variant and Granzyme H variant is one having at least 95% amino acid sequence identity to Granzyme B and Granzyme H amino acid sequences.

The invention also encompasses polynucleotides which encode Granzyme B variants and Granzyme H variants. Accordingly, any nucleic acid sequence which encodes the amino acid sequence of Granzyme B variants and Granzyme H variants can be used to produce recombinant molecules which express Granzyme B variants and Granzyme H variants. In a particular embodiment, the invention encompasses the polynucleotide comprising the nucleic acid sequence of SEQ ID NOS: 1-5.

It will be appreciated by those skilled in the art that as a result of the degeneracy of the genetic code, a multitude of nucleotide sequences encoding Granzyme B variants and Granzyme H variants, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring Granzyme B variants and Granzyme H variants, and all such variations are to be considered as being specifically disclosed.

Although nucleotide sequences which encode Granzyme B and Granzyme H and its variants are preferably capable of hybridizing to the nucleotide sequence of the naturally occurring Granzyme B variants and Granzyme H variants under appropriately selected conditions of stringency, it may be advantageous to produce nucleotide sequences encoding Granzyme B variants and Granzyme H variants or their derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding Granzyme B variants and Granzyme H variants and their derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode Granzyme B variants and Granzyme H variants and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding Granzyme B variants and Granzyme H variants or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399-407) and Kimmel, A. R. (1987; Methods Enzymol. 152:507-511).

Methods for DNA sequencing which are well known and generally available in the art and may be used to practice any of the embodiments of the invention. The methods may employ such enzymes as the Klenow fragment of DNA polymerase I, Sequenase® (U.S. Biochemical Corp, Cleveland, Ohio), Tag polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding Granzyme B variants and Granzyme H variants may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318-322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22-30 nucleotides in length, to have a GC content of 50% or more, and to anneal to the target sequence at temperatures about 68.degree.-72.degree. C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111-119). In this method, multiple restriction enzyme digestions and ligations may also be used to place an engineered double-stranded sequence into an unknown fragment of the DNA molecule before performing PCR Another method which may be used to retrieve unknown sequences is that of Parker, J. D. et al. (1991; Nucleic Acids Res. 19:3055-3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode Granzyme B variants and Granzyme H variants may be used in recombinant DNA molecules to direct expression of Granzyme B variants and Granzyme H variants, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express Granzyme B variants and Granzyme H variants.

As will be understood by those of skill in the art, it may be advantageous to produce Granzyme B variants and Granzyme H variants-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter Granzyme B variants and Granzyme H encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding Granzyme B variants and Granzyme H variants may be ligated to a heterologous sequence to encode a fusion protein. For example, to screen peptide libraries for inhibitors of Granzyme B and Granzyme H activity, it may be useful to encode chimeric Granzyme B variant and Granzyme H variant proteins that can be recognized by a commercially available antibody. A fusion protein may also be engineered to contain a cleavage site located between the Granzyme B variant and Granzyme H variant encoding sequence and the heterologous protein sequence, so that Granzyme B variant and Granzyme H variant may be cleaved and purified away from the heterologous moiety.

In another embodiment, sequences encoding Granzyme B variants and Granzyme H variants may be synthesized, in whole or in part, using chemical methods well known in the art (see Caruthers, M. H. et al. (1980) Nucl. Acids Rs. Symp. Ser. 215-223, Horn, T. et al. (1980) Nucl. Acids Rs. Symp. Ser. 215225-232). Alternatively, the protein itself may be produced using chemical methods to synthesize the amino acid sequence of Granzyme B variants and Granzyme H variants, or a fragment thereof. For example, peptide synthesis can be performed using various solid-phase techniques (Roberge, J. Y. et al. (1995) Science 269:202-204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) Proteins, Structures and Molecular Principles, WH Freeman and Co., New York, N.Y.). The composition of the synthetic peptides may be confirmed by amino acid analysis or sequencing (e.g., the Edman degradation procedure; Creighton, supra). Additionally, the amino acid sequence of Granzyme B variants and Granzyme H variants, or any part thereof, may be altered during direct synthesis and/or combined using chemical methods with sequences from other proteins, or any part thereof, to produce a variant polypeptide.

In order to express a biologically active Granzyme B variant and Granzyme H variant, the nucleotide sequences encoding Granzyme B variant and Granzyme H variant or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding Granzyme B variants and Granzyme H variants and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N. Y., and Ausubel, F. M. et al. (1989) Current Protocols in Molecular Biology, John Wiley & Sons, New York, N.Y.

A variety of expression vector/host systems may be utilized to contain and express sequences encoding Granzyme B variants and Granzyme H variants. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

In mammalian host cells, a number of viral-based expression systems may be utilized. In cases where an adenovirus is used as an expression vector, sequences encoding Granzyme B variants and Granzyme H variants may be ligated into an adenovirus transcription/translation complex consisting of the late promoter and tripartite leader sequence. Insertion in a non-essential E1 or E3 region of the viral genome may be used to obtain a viable virus which is capable of expressing Granzyme B variants and Granzyme H variants in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

For long-term, high-yield production of recombinant proteins, stable expression is preferred. For example, cell lines which stably express Granzyme B variants and Granzyme H variants may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Although the presence/absence of marker gene expression suggests that the gene of interest is also present, its presence and expression may need to be confirmed. For example, if the sequence encoding Granzyme B variants and/or Granzyme H variants is inserted within a marker gene sequence, transformed cells containing sequences encoding Granzyme B variants and Granzyme H variants can be identified by the absence of marker gene function. Alternatively, a marker gene can be placed in tandem with a sequence encoding Granzyme B variants and Granzyme H variants under the control of a single promoter. Expression of the marker gene in response to induction or selection usually indicates expression of the tandem gene as well.

Alternatively, host cells which contain the nucleic acid sequence encoding Granzyme B variants and Granzyme H variants and express Granzyme B variants and Granzyme H variants may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding Granzyme B variants and Granzyme H variants can be detected by DNA-DNA or DNA-RNA hybridization or amplification using probes or fragments or fragments of polynucleotides encoding Granzyme B variants and Granzyme H variants. Nucleic acid amplification based assays involve the use of oligonucleotides or oligomers based on the sequences encoding Granzyme B variants and Granzyme H variants to detect transformants containing DNA or RNA encoding Granzyme B variants and Granzyme H variants.

A variety of protocols for detecting and measuring the expression of Granzyme B variants and Granzyme H variants, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on Granzyme B variants and Granzyme H variants is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211-1216).

A wide variety of labels and conjugation techniques are known by those skilled in the art and may be used in various nucleic acid and amino acid assays. Means for producing labeled hybridization or PCR probes for detecting sequences related to polynucleotides encoding Granzyme B variants and Granzyme H variants include oligolabeling, nick translation, end-labeling or PCR amplification using a labeled nucleotide. Alternatively, the sequences encoding Granzyme B variants and Granzyme H variants, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding Granzyme B variants and Granzyme H variants may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode Granzyme B variants and Granzyme H variants may be designed to contain signal sequences which direct secretion of Granzyme B variants and Granzyme H variants through a prokaryotic or eukaryotic cell membrane. Other constructions may be used to join sequences encoding Granzyme B variants and Granzyme H variants to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and Granzyme B variants and Granzyme H variants may be used to facilitate purification. One such expression vector provides for expression of a fusion protein containing Granzyme B variants and Granzyme H variants and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263-281) while the enterokinase cleavage site provides a means for purifying Granzyme B variants and Granzyme H variants from the fusion protein. A discussion of vectors which contain fusion proteins is provided in Kroll, D. J. et al. (1993; DNA Cell Biol. 12:441-453).

In addition to recombinant production, fragments of Granzyme B variants and Granzyme H variants may be produced by direct peptide synthesis using solid-phase techniques Merrifield J. (1963) J. Am. Chem. Soc. 85:2149-2154). Protein synthesis may be performed using manual techniques or by automation. Automated synthesis may be achieved, for example, using Applied Biosystems 431A Peptide Synthesizer (Perkin Elmer). Various fragments of Granzyme B variants and Granzyme H variants may be chemically synthesized separately and combined using chemical methods to produce the full length molecule.

In one embodiment, Granzyme B variants and Granzyme H variants or a fragment or derivative thereof may be administered to a subject to treat a developmental disorder. The term "developmental disorder" refers to any disorder associated with development or function of a tissue, organ, or system of a subject, i.e., brain, adrenal gland, kidney, skeletal or reproductive system.

In another embodiment, Granzyme B variants and Granzyme H variants or a fragment or derivative thereof may be administered to a subject to treat a neoplastic disorder. Such disorders may include, but are not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of Granzyme B variants and Granzyme H variants may be produced using methods which are generally known in the art. In particular, purified Granzyme B variants and Granzyme H variants may be used to produce antibodies or to screen libraries of pharmaceutical agents to identify those which specifically bind Granzyme B variants and Granzyme H variants.

Antibodies to Granzyme B variants and Granzyme H variants may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

It is preferred that the oligopeptides, peptides, or fragments used to induce antibodies to Granzyme B variants and Granzyme H variants have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of Granzyme B variants and Granzyme H variants amino acids may be fused with those of another protein such as keyhole limpet hemocyanin and antibody produced against the chimeric molecule.

Monoclonal antibodies to Granzyme B variants and Granzyme H variants may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495-497; Kozbor, D. et al. (1985) J. Immunol. Methods 81:31-42; Cote, R. J. et al. (1983) Proc. Natl. Acad. Sci. 80:2026-2030; Cole, S. P. et al. (1984) Mol. Cell Biol. 62:109-120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851-6855; Neuberger, M. S. et al. (1984) Nature 312:604-608; Takeda, S. et al. (1985) Nature 314:452-454). Alternatively, techniques described for the production of single chain antibodies may be adapted, using methods known in the art, to produce Granzyme B variants and Granzyme H variants-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120-3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86:3833-3837; Winter, G. et al. (1991) Nature 349:293-299).

Antibody fragments which contain specific binding sites for Granzyme B variants and Granzyme H variants may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275-1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between Granzyme B variants and Granzyme H variants and its specific antibody. A two-site, monoclonal-based immunoassay utilizing monoclonal antibodies reactive to two non-interfering Granzyme B variants and Granzyme H variants epitopes is preferred, but a competitive binding assay may also be employed (Maddox, supra).

In another embodiment of the invention, the polynucleotides encoding Granzyme B variants and Granzyme H variants, or any fragment or complement thereof, may be used for therapeutic purposes. In one aspect, the complement of the polynucleotide encoding Granzyme B variants and Granzyme H variants may be used in situations in which it would be desirable to block the transcription of the mRNA. In particular, cells may be transformed with sequences complementary to polynucleotides encoding Granzyme B variants and Granzyme H variants. Thus, complementary molecules or fragments may be used to modulate Granzyme B variants and Granzyme H variants activity, or to achieve regulation of gene function. Such technology is now well known in the art, and sense or antisense oligonucleotides or larger fragments, can be designed from various locations along the coding or control regions of sequences encoding Granzyme B variants and Granzyme H variants.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding Granzyme B variants and Granzyme H variants. These techniques are described both in Sambrook et al. (supra) and in Ausubel et al. (supra).

Genes encoding Granzyme B variants and Granzyme H variants can be turned off by transforming a cell or tissue with expression vectors which express high levels of a polynucleotide or fragment thereof which encodes Granzyme B variants and Granzyme H variants. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding Granzyme B variants and Granzyme H variants (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, Molecular and Immunologic Approaches, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding Granzyme B variants and Granzyme H variants.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding Granzyme B variants and Granzyme H variants. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462-66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of Granzyme B variants and Granzyme H variants, antibodies to Granzyme B variants and Granzyme H variants, mimetics, agonists, antagonists, or inhibitors of Granzyme B variants and Granzyme H variants. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example Granzyme B variants and Granzyme H variants or fragments thereof, antibodies of Granzyme B variants and Granzyme H variants, agonists, antagonists or inhibitors of Granzyme B variants and Granzyme H variants, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

In another embodiment, antibodies which specifically bind Granzyme B variants and Granzyme H variants may be used for the diagnosis of conditions or diseases characterized by expression of Granzyme B variants and Granzyme H variants, or in assays to monitor patients being treated with Granzyme B variants and Granzyme H variants, agonists, antagonists or inhibitors. The antibodies useful for diagnostic purposes may be prepared in the same manner as those described above for therapeutics. Diagnostic assays for Granzyme B variants and Granzyme H variants include methods which utilize the antibody and a label to detect Granzyme B variants and Granzyme H variants in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring Granzyme B variants and Granzyme H variants are known in the art and provide a basis for diagnosing altered or abnormal levels of Granzyme B variants and Granzyme H variants expression. Normal or standard values for Granzyme B variants and Granzyme H variants expression are established by combining body fluids or cell extracts taken from normal mammalian subjects, preferably human, with antibody to Granzyme B variants and Granzyme H variants under conditions suitable for complex formation. The amount of standard complex formation may be quantified by various methods, but preferably by photometric means. Quantities of Granzyme B variants and Granzyme H variants expressed in subject samples, control and disease, from biopsied tissues are compared with the standard values. Deviation between standard and subject values establishes the parameters for diagnosing disease.

In another embodiment of the invention, the polynucleotides encoding Granzyme B variants and Granzyme H variants may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of Granzyme B variants and Granzyme H variants may be correlated with disease. The diagnostic assay may be used to distinguish between absence, presence, and excess expression of Granzyme B variants and Granzyme H variants, and to monitor regulation of Granzyme B variants and Granzyme H variants levels during therapeutic intervention.

In one aspect, hybridization with PCR probes which are capable of detecting polynucleotide sequences, including genomic sequences, encoding Granzyme B variants and Granzyme H variants or closely related molecules, may be used to identify nucleic acid sequences which encode Granzyme B variants and Granzyme H variants. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding Granzyme B variants and Granzyme H variants, alleles, or related sequences.

Probes may also be used for the detection of related sequences, and should preferably contain at least 50% of the nucleotides from any of the Granzyme B variants and Granzyme H variants encoding sequences. The hybridization probes of the subject invention may be DNA or RNA and derived from the nucleotide sequence of SEQ ID NO:2 or from genomic sequence including promoter, enhancer elements, and introns of the naturally occurring Granzyme B variants and Granzyme H variants.

Means for producing specific hybridization probes for DNAs encoding Granzyme B variants and Granzyme H variants include the cloning of nucleic acid sequences encoding Granzyme B variants and Granzyme H variants or Granzyme B variants and Granzyme H variants derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

In a particular aspect, the nucleotide sequences encoding Granzyme B variants and Granzyme H variants may be useful in assays that detect activation or induction of various cancers. The nucleotide sequences encoding Granzyme B variants and Granzyme H variants may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding Granzyme B variants and Granzyme H variants in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of Granzyme B variants and Granzyme H variants, a normal or standard profile for expression is established. This may be accomplished by combining body fluids or cell extracts taken from normal subjects, either animal or human, with a sequence, or a fragment thereof, which encodes Granzyme B variants and Granzyme H variants, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding Granzyme B variants and Granzyme H variants may involve the use of PCR. Such oligomers may be chemically synthesized, generated enzymatically, or produced in vitro. Oligomers will preferably consist of two nucleotide sequences, one with sense orientation (5'→3') and another with antisense (3'→5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of Granzyme B variants and Granzyme H variants include radiolabeling or biotinylating nucleotides, coamplification of a control nucleic acid, and standard curves onto which the experimental results are interpolated (Melby, P. C. et al. (1993) J. Immunol. Methods, 159:235-244; Duplaa, C. et al. (1993) Anal. Biochem. 229-212:236). The speed of quantitation of multiple samples may be accelerated by running the assay in an ELISA format where the oligomer of interest is presented in various dilutions and a spectrophotometric or calorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150-55).

In one embodiment, the microarray is prepared and used according to the methods described in PCT application WO95/11995 (Chee et al.), Lockhart, D. J. et al. (1996; Nat. Biotech. 14:1675-1680) and Schena, M. et al. (1996; Proc. Natl. Acad. Sci. 93:10614-10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6-60 nucleotides in length, more preferably 15-30 nucleotides in length, and most preferably about 20-25 nucleotides in length. For a certain type of microarray, it may be preferable to use oligonucleotides which are only 7-10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs"

will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode Granzyme B variants and Granzyme H variants may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127-134, and Trask, B. J. (1991) Trends Genet. 7:149-154.

In additional embodiments, the nucleotide sequences which encode Granzyme B variants and Granzyme H variants may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

Example

Isolation of Peripheral Blood Mononuclear Cells (PBMC) and RNA

PBMC were isolated from whole blood using Ficoll-Hypaque density gradient centrifugation. These cells were suspended in Trizol reagent (GIBCO-BRL, Rockville, Md.). Total RNA was isolated immediately according to the manufacturer's instructions. Poly (A)$^+$ RNA was isolated from total RNA by using Oligo-Tex mini mRNA kit (Qiagen, Valencia, Calif.) according to the manufacturer's recommendations. Patient samples were obtained on an IRB approved protocol. None of the patients were receiving treatment at the time blood samples were collected.

Activation of PBMC

Normal PBMC were cultured in vitro and activated by phytohemagglutinin (PHA, Sigma Chemical Co. St. Louis, Mo.) (1 µg/ml, 2 days) and Interleulcin-2 (IL-2) (100 U/ml, 10 days), then total RNA was isolated as described above.

Microarray Analysis cDNA Microarray probing and analysis was performed by IncyteGenomics as described previously (Kothapalli et al, 2002). Oligonucleotide microarray was performed by using HU 6800 obtained from Affymetrix (Santa Clara, Calif.) as described previously (Kothapalli et al. 2002).

Library Construction and Screening cDNA was synthesized from poly(A)$^+$ RNA isolated from pooled PBMC of seven LGL leukemia patients using an oligo dT primer. The cDNA was uni-directionally inserted at the EcoRI/XhoI sites of Lambda ZAPII (Stratagene). These cDNA libraries were plated at a density of 50,000 plaque-forming units per 150 mm plate. Following incubation for 8 h at 37° C., the plated phage was overlaid with nitrocellulose filters. After 1 min the filters were removed and the membranes were crossed linked by auto cross-linker. A [$^{32}$P] labeled cDNA fragment derived from the 3' end of granzyme H (GenBank Accession No. M 57888) was used to probe the filters. Hybridizations, washings and exposure of the membranes to films for colony screening were then performed as outlined in the standard methodology. Secondary and tertiary screenings were also performed as outlined in standard methodology. After isolation of pure phage containing the gene of interest, mini- or maxi-preparations were made to isolate plasmid cDNA containing the gene of interest.

RT-PCR

The following primers were designed based on the sequence information obtained by screening a LGL leukemia library. GRN 13 F "TGCAACCAATCCTGC TTC" (SEQ ID NO: 6) was used as the forward and GRBR "AGAGAAG-GTGT TTCAT CACAG" (SEQ ID NO: 7) as the reverse primer to amplify granzyme B and its variants, granzyme 16 F "TTTGTGCT GA CAGCTGCTCAC TGT" (SEQ ID NO: 8) was used as the forward primer and granzyme 16R "GGAAGGTTAG TCT CATGCC TGCTG TT A" (SEQ ID NO: 9) was used as the reverse primer to amplify Granzyme H alternative splice variants. Total RNA isolated from PBMC of LGL leukemia patients and normal healthy individuals was utilized for making cDNA using reverse transcriptase with either oligo(dT) primer or with random healers. The PCR mixture was heated to 95° C. for 2 min and cycled 40 times at 95° C. for 30 sec, 60° C. for 45 sec, 72° C. for 1.5 min. Finally the reaction mixture was heated at 72° C. for 7 mm and stored at 4° C. The reaction products were electrophoresed on 1% agarose gels and the bands were excised and cloned into a TOPO-TA cloning vector (Invitrogen, Carlsbad, Calif.) and sequenced.

Figure 2:
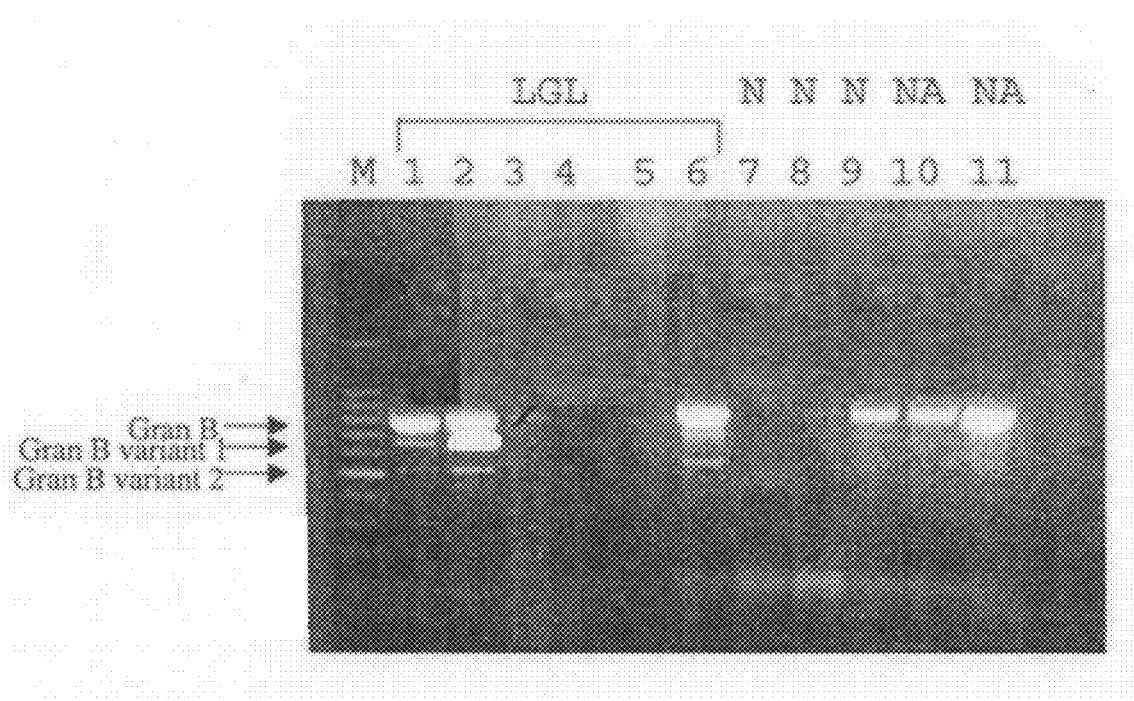
FIG. 2 represents the RT-PCR analysis of Granzyme B and variants. RT-PCR was performed using primers GEN 13 F "TGCAACCAATCCTGCTTC" (SEQ ID NO: 6) as forward primer, and GBBR "AGAGAAGGTGTTTCATCACAG" (SEQ ID NO: 7) as reverse primer. M=DNA markers, Lanes 1, 2, 3, 4, 5 and 6 PCR were products for LGL leukemia patients. Lane 7, 8 and 9 were PCR products from normal PBMCs and Lane 10 and 11 were PCR products from normal activated PBMCs.
Figure 3:
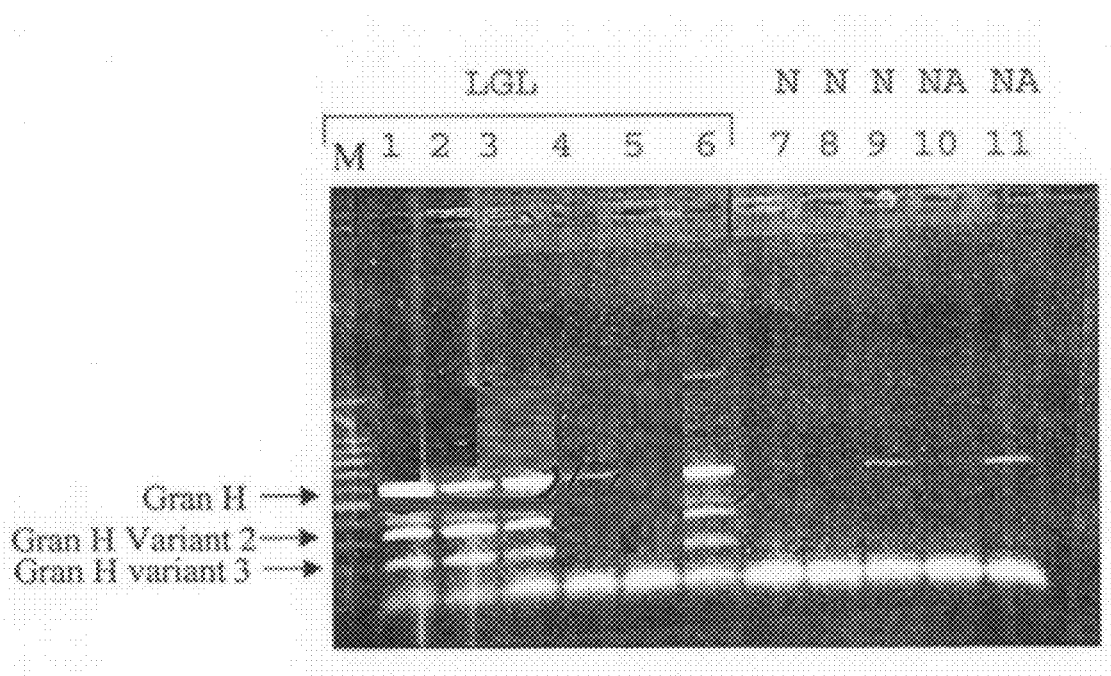
FIG. 3 represents the RT-PCR analysis of Granzyme H and variants. RT-PCR was performed using primers Granzyme, clone 16 "TTTGTGCTGACAGCTGCTCACTGT" (SEQ ID NO: 8) as forward primer, and Granzyme 16R "GGAAGGT-TAGTCTCATGCCTGCTGTTA" (SEQ ID NO: 9) as reverse primer. M=DNA markers, Lanes 1, 2, 3, 4, 5 and 6 PCR were products for LGL leukemia patients. Lane 7, 8 and 9 were PCR products from normal PBMCs and Lane 10 and 11 were PCR products from normal activated PBMCs.

Both cDNA microarray and oligonucleotide array demonstrated up-regulation of granzyme B and granzyme H. As the inventor's reported previously, the 1.2 kb fragment spotted on the cDNA microarray as granzyme B was cross reactive with granzyme B and granzyme H. Northern blot analysis exhibited a broad band suggesting the possibility of different forms of granzymes (Kothapalli et al., 2003). By using gene-specific probes in an RNase protection assay, the inventors were able to demonstrate the over-expression of both granzyme B and granzyme H in leukemic LGL cells. The inventor's LGL leukemia cDNA library was probed with the 1.2 kb granzyme H fragment to identify different forms of granzymes. The inventor's selected several positive clones and sequenced them. In addition to full-length sequences of granzymes B and H, two variants were identified. One was very similar to granzyme B with ten additional nucleotides, SEQ ID NO: 1 (FIG. 1), and the other one was similar to granzyme H but missing exon 3 (SEQ ID NO: 4). In order to confirm the presence of these variants in leukemic LGL, the inventor's carried out RT-PCR using RNA isolated from normal PBMCs, normal PBMC activated with IL2 and PHA, and from LGL leukemia patients. The primers designed to amplify granzyme B yielded several bands on the gels (FIG. 2). Similarly, primers designed to amplify granzyme H resulted in several bands (FIG. 3).

These bands were cut and cloned into TA vectors and sequenced. Sequencing of the clones revealed the existence of several splice variants of granzyme B and granzyme H. In one of the splice variants of granzyme B (Granzyme B Variant 1), exon 3 was deleted (SEQ ID NO: 2) whereas in another splice variant (Granzyme B Variant 2), exon two and three were deleted (SEQ ID NO: 3). The inventors identified three splice variants for Granzyme H (FIG. 3). The inventor's characterized two of these splice variants: in one (Granzyme H Variant 2), exon 3,4 was missing as identified by screening the library (SEQ ID NO: 4) and in another (Granzyme H Variant 3), exon 4 was deleted. (SEQ ID NO: 5).

Cell-mediated killing by cytotoxic T lymphocytes (CTL) is a major defense mechanism of the organism against virus infected cells, tumor progression and transplanted tissue. CTLs recognize foreign antigens on the surface of target cells, bind to them and releasing various cytotoxic molecules such as granzymes and perform. These molecules are from the granules which lysis the target cells (Russell and Ley, 2002). In humans, serine proteases such as granzyme A, B and the pore-forming protein perform a critical role in target cell death (Shresta et al, 1998). All granzymes are synthesized in the form of zymogens that are inactive. After removal of signal peptides by signal peptidase and dipeptides by dipeptidyl-transferase I, these granzymes become active and stored in the granules (Jenne and Tschopp, 1988, Pham and Ley, 1999). At this stage granzymes are functionally able to kill the target cells. It was previously established that granzymes are essential components of cell-mediated cytotoxicity (Russell and Ley, 2002). Granzyme deficiencies and mutations leading to functional defects of the granzymes have not been identified in humans. However, two cryptic splice sites generating aberrant mRNA transcripts for granzyme B have been identified (Klein et al, 1989).

Figure 4:
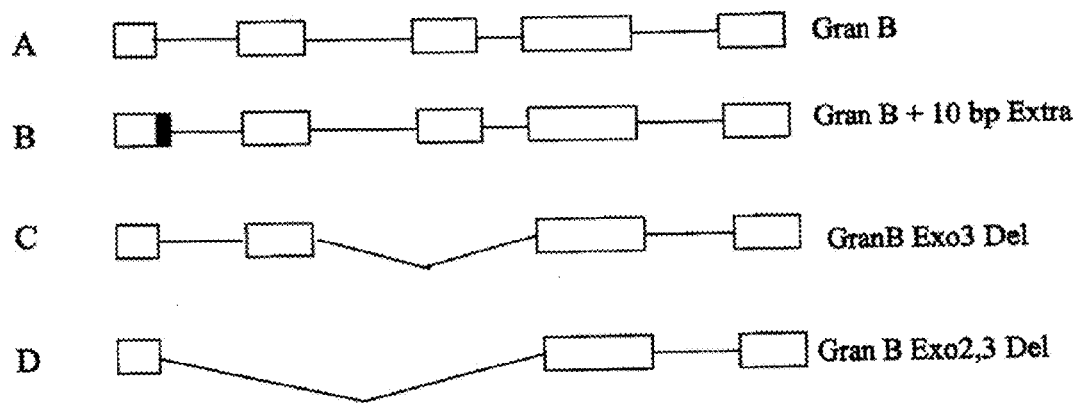
FIG. 4A-D is a schematic diagram showing alternative splice variants of Granzyme B.
Figure 5:
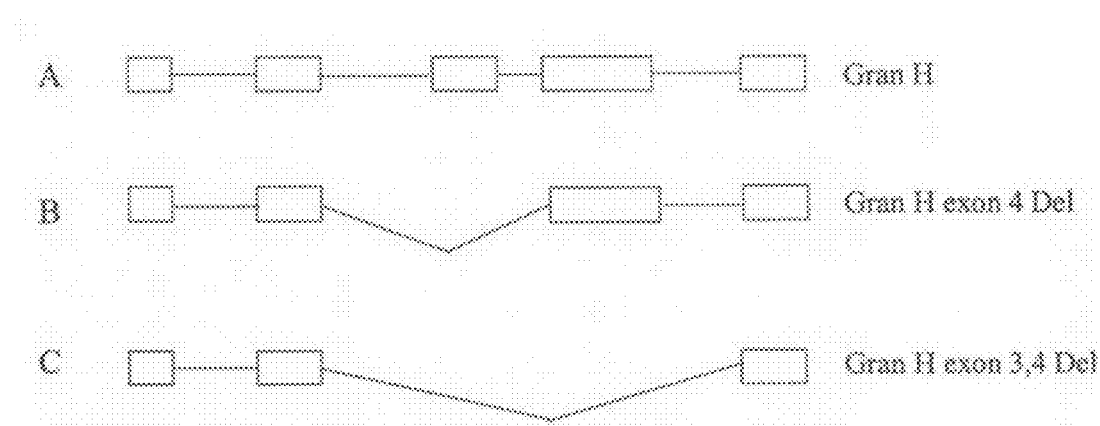
FIG. 5A-C is a schematic diagram showing alternative splice variants of Granzyme H.

The inventors have identified several alternative splice variants for granzyme B and granzyme H. These are constitutively expressed in LGL leukemia patients. Schematic diagrams displaying different variants were shown in FIGS. 4 and 5. These splice variants were also observed when PBMCs were activated with 1L2 and PHA. An insertion of 10 nucleotides from intron I altered the open reading frame of granzyme B that leads to altered signal peptide. Difficulties in cleaving the altered signal peptide from the nascent protein might result in accumulation of inactive granzyme B.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be the to fall therebetween. Now that the invention has been described,

What is claimed is:

1. A method of diagnosing large granular lymphocyte leukemia in a patient comprising: isolating RNA from a sample of the patient; generating cDNA from the isolated RNA; hybridizing a gene-specific probe selected from the group consisting of SEQ NO: 8 and SEQ ID NO: 9 to the cDNA wherein the probe is specific for detecting polynucleotide sequences encoding at least one granzyme H variant or fragment thereof having a sequence selected from the group consisting of SEQ ID NO: 4 and SEQ ID NO:5; determining an expression level of the at least one granzyme H variant in the sample from the patient; comparing the expression level of the at least one granzyme H variant from the patient to a predetermined control expression level; wherein an overexpression of the at least one granzyme H variant in the sample as compared to the control expression level is indicative of a diagnosis of large granular lymphocyte leukemia.

2. The method of claim 1, wherein the granzyme H variant is a polynucleotide having SEQ ID NO: 4.

3. The method of claim 1, wherein the granzyme H variant is a polynucleotide having SEQ ID NO: 5.

4. The method of claim 1, wherein the probe is labeled with a reporter molecule.

* * * * *